US 9,244,032 B2

(12) United States Patent
Kitanoya et al.

(10) Patent No.: US 9,244,032 B2
(45) Date of Patent: Jan. 26, 2016

(54) GAS DETECTING APPARATUS AND GAS DETECTING METHOD

(75) Inventors: Shoji Kitanoya, Kasugai (JP); Masahiro Yamashita, Komaki (JP); Masaya Watanabe, Komaki (JP); Daisuke Ichikawa, Kani (JP)

(73) Assignee: NGK SPARK PLUG CO., LTD., Aichi (JP)

(*) Notice: Subject to any disclaimer, the term of this patent is extended or adjusted under 35 U.S.C. 154(b) by 888 days.

(21) Appl. No.: 13/432,764

(22) Filed: Mar. 28, 2012

(65) Prior Publication Data

US 2012/0247184 A1 Oct. 4, 2012

(30) Foreign Application Priority Data

Mar. 28, 2011 (JP) .................................. 2011-070291

(51) Int. Cl.
*G01N 27/18* (2006.01)
(52) U.S. Cl.
CPC ...................................... *G01N 27/18* (2013.01)
(58) Field of Classification Search
CPC .............................. G01N 27/18; G01N 33/005
See application file for complete search history.

(56) References Cited

FOREIGN PATENT DOCUMENTS

| JP | 5-77759 U | 10/1993 |
| JP | 9-5283 A | 1/1997 |
| JP | 95284 A | 1/1997 |
| JP | 11-183422 A | 7/1999 |
| JP | 2007-57353 A | 3/2007 |

OTHER PUBLICATIONS

English translation of JP 09-005284: Description, retrieved on Dec. 17, 2014 at <http://www4.ipdl.inpit.go.jp/Tokujitu/PAJdetail.ipdl?N0000=60&N0120=01&N2001=2&N3001=H09-005284>.*
Office Action, dated Dec. 10, 2013, issued by the Japanese Patent Office in counterpart Japanese Patent Application No. 2011-070291.

* cited by examiner

*Primary Examiner* — Lisa Caputo
*Assistant Examiner* — Punam Roy
(74) *Attorney, Agent, or Firm* — Sughrue Mion, PLLC

(57) ABSTRACT

A gas detecting apparatus including: a heating resistor exposed to a detected atmosphere, and a control circuit for controlling the heating resistor at two different temperatures, wherein each output voltage from the heating resistor corresponding to the different temperatures is detected when the heating resistor is controlled to the different temperatures, and a state of a gas is obtained based on the detected output voltage. For example, two different offset voltages are set, each potential difference obtained by subtracting each of the offset voltages from corresponding detected output voltages is amplified and the state of the gas is obtained using the amplified potential differences.

4 Claims, 8 Drawing Sheets

GAS DETECTING APPARATUS AND GAS DETECTING METHOD

BACKGROUND OF THE INVENTION

1. Field of the Invention

The present invention relates to a gas detecting apparatus capable of being used in detection of a state of a gas, for example, concentration measurement or leak detection of a combustible gas present in a detected atmosphere, or detection of the humidity of the detected atmosphere.

2. Description of the Related Art

As a gas detecting apparatus, for example, a heat conductivity humidity sensor is known in the related art. Such a heat conductivity humidity sensor is a sensor for measuring humidity using a change in thermal radiation from a temperature measurement resistor heated by a heating element for self-heating by Joule heat.

As this kind of heat conductivity humidity sensor, a technique for switching and controlling a heating resistor at two temperatures using a Wheatstone bridge circuit and obtaining humidity from a voltage applied to a heater at that time has been disclosed in recent years (see Patent Reference 1).

[Patent Reference 1] JP-A-H09-5284

3. Problems to be Solved by the Invention

However, in the related-art technique described above, an output voltage from both ends of the heating resistor is directly inputted to an arithmetic circuit (microcomputer), so that there is a problem that a resolution of the output voltage (measured voltage) is limited by an input resolution of the arithmetic circuit.

That is, in the heat conductivity humidity sensor using the heating resistor, since it is necessary to detect a very small change in voltage, there is a problem that measurement accuracy becomes low when the resolution of the measured voltage is low.

As a countermeasure, it is contemplated to use an arithmetic circuit having high resolution, but there is generally a problem that the high resolution also increases the price of the arithmetic circuit.

It is contemplated to amplify the measured voltage by an amplifier. However, since it is necessary to set the voltage after amplification at a power supply voltage or less, an amplification factor cannot be increased too much. This results in a problem that high measurement accuracy cannot be obtained.

SUMMARY

The invention has been implemented to solve the problems described above, and other disadvantages not described above. Also, the present invention is not required to overcome the problems described above, and an illustrative embodiment may not overcome any of the problems described above. An object of the invention is to provide a gas detecting apparatus with high measurement accuracy while using an inexpensive device with low input resolution, in a case of detecting a gas state such as concentration or humidity of a specified gas such as a combustible gas.

According to an aspect of the invention, there is provided a gas detecting apparatus including: a heating resistor exposed to an atmosphere; and a control circuit for controlling the heating resistor to exhibit two different temperatures, wherein the control circuit detects output voltages from the heating resistor corresponding to the two different temperatures, wherein potential differences, which are obtained by subtracting respective ones of two different offset voltages from corresponding ones of the detected output voltages, are amplified, and wherein the control circuit detects a state of a gas in the atmosphere using the amplified potential differences.

Since an illustrative embodiment of the invention has a configuration of controlling the heating resistor at the two different temperatures (set temperatures), two different offset voltages are set. Each potential difference obtained by subtracting each of the offset voltages from each of the output voltages from the heating resistor corresponding to the different temperatures is amplified, and the state of the gas, such as concentration or humidity of the gas, is obtained based on each amplified potential difference. Accordingly, even when the output voltage from the heating resistor has a very small change in voltage, it is possible to amplify at a large amplification factor by suitably taking out only the portion of change in voltage.

Hence, there is a remarkable effect of the capability of measuring the state of the gas with high accuracy by setting a large amplification factor even in the case of using a low-cost electronic controller such as a microcomputer.

That is, even in the case of using an inexpensive device with low input resolution, an illustrative embodiment of the invention can detect the state of the gas at high resolution and has a remarkable effect of improving measurement accuracy of the state of the gas.

The gas detecting apparatus may further include a first offset setting unit which sets a first offset voltage of the two different offset voltages, the first offset voltage corresponding to a first temperature of the two different temperatures; a second offset setting unit which sets a second offset voltage of the two different offset voltages, the second offset voltage corresponding to a second temperature of the two different temperatures; a first amplifying unit which amplifies a first potential difference between the first offset voltage and a first output voltage of the detected output voltages, the first output voltage corresponding to the first temperature; and a second amplifying unit which amplifies a second potential difference between the second offset voltage and a second output voltage of the detected output voltages, the second output voltage corresponding to the second temperature.

Since an illustrative embodiment of the invention includes the first offset setting unit and the first amplifying unit, and the second offset setting unit and the first amplifying unit in correspondence with the two temperatures (hence, the two offset voltages), the offset voltages corresponding to the respective temperatures (set temperatures) can always be set to the first and second amplifying unit as compared with the case of, for example, adopting a configuration of switching to two different offset voltages using an electronic controller such as a microcomputer in a circuit including one amplifying unit. Also, amplification factors (amplification degrees) of the amplifying unit can be set individually at different values. This enables measurement of the state of the gas with higher accuracy. Also, there is an advantage of the capability of simplifying control of the electronic controller such as the microcomputer since the need for switching control etc., of the offset voltages is eliminated.

The gas detecting apparatus may further include an amplifying unit, wherein an input offset voltage that is input to the amplifying unit may be switched to any of the two different offset voltages in response to a control signal from an electronic controller.

In an illustrative embodiment of the invention, the offset voltage inputted to one amplifying unit is switched to the two different offset voltages based on the control signal from the electronic controller (for example, the microcomputer), so that it is unnecessary to form an offset voltage setting unit corresponding to the respective temperatures and the configuration can be simplified. Consequently, there are advantages of the capability of measuring the state of the gas with high accuracy while minimizing a circuit size and reducing cost.

DESCRIPTION OF REFERENCE NUMERALS AND SIGNS

Figure 1:
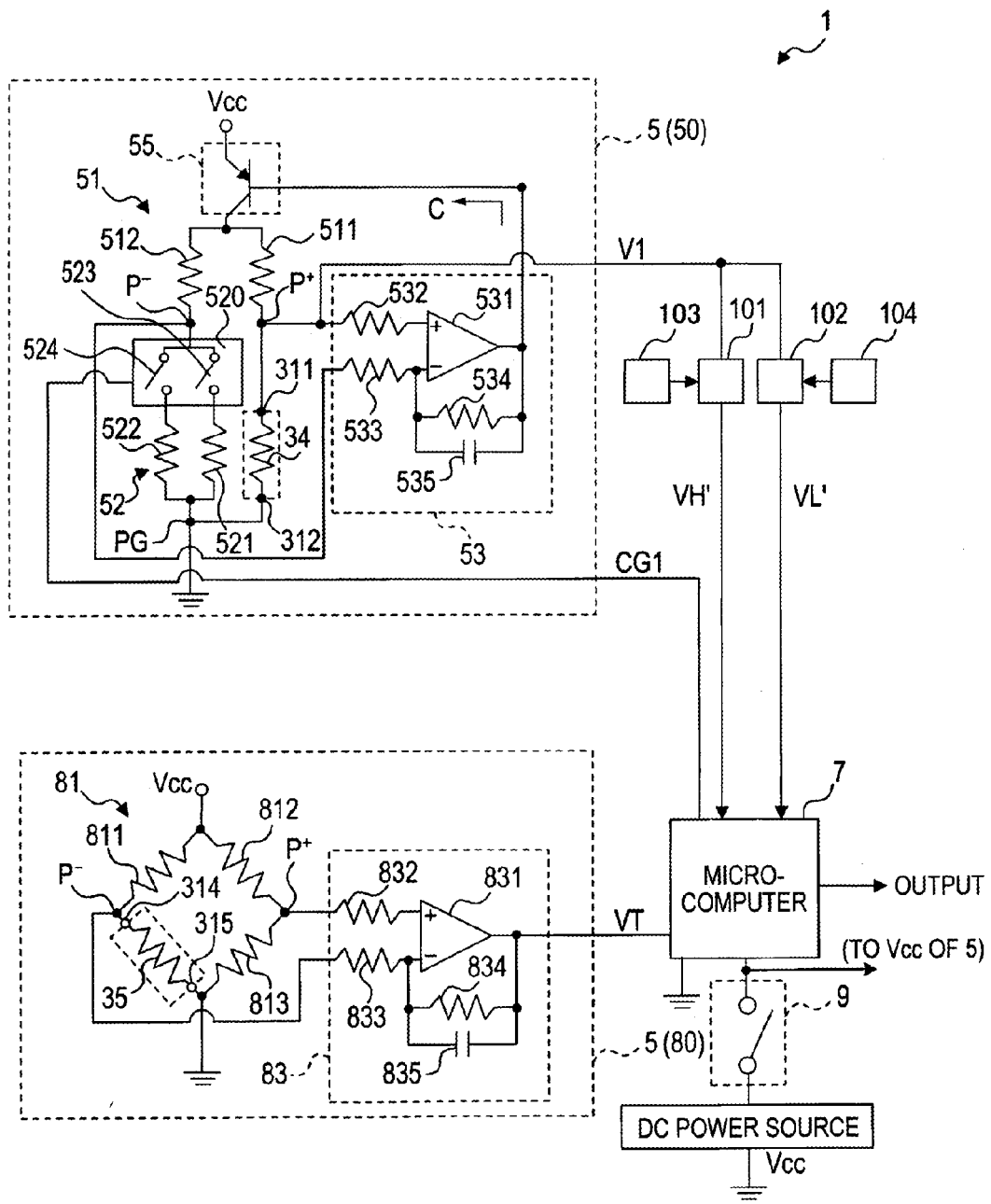
FIG. 1 is a configuration diagram of a combustible gas detecting apparatus of a first embodiment.

Reference numerals used to indicate various structural features in the drawings include:
1,110,150 COMBUSTIBLE GAS DETECTING APPARATUS
3 GAS DETECTING ELEMENT
5 CONTROL CIRCUIT
7,140,180 MICROCOMPUTER
9 STARTING SWITCH
34 HEATING RESISTOR
35 TEMPERATURE MEASUREMENT RESISTOR
50 ENERGIZATION CONTROL CIRCUIT
51 BRIDGE CIRCUIT
55 CURRENT REGULATING CIRCUIT
57 SWITCHING CIRCUIT
80 TEMPERATURE REGULATING CIRCUIT
81 BRIDGE CIRCUIT
87 SWITCHING CIRCUIT
101 FIRST AMPLIFYING CIRCUIT
102 SECOND AMPLIFYING CIRCUIT
103 FIRST OFFSET CIRCUIT
104 SECOND OFFSET CIRCUIT
120,160 OFFSET CIRCUIT
130,170 AMPLIFYING CIRCUIT
CH FIRST SET TEMPERATURE
CL SECOND SET TEMPERATURE
TW CYCLE TIME

DETAILED DESCRIPTION

Illustrative embodiments of the invention will hereinafter be described along with the drawings. However, the present invention should not be construed as being limited thereto.

First Embodiment

Hereinafter, a gas detecting apparatus will be described by taking, as an example, a combustible gas detecting apparatus for detecting concentration of a combustible gas such as a hydrogen gas.

First, a basic configuration of the combustible gas detecting apparatus of the present embodiment will be described.

In addition, FIG. 1 is a configuration diagram of a combustible gas detecting apparatus 1 to which an illustrative embodiment of the invention is applied. FIGS. 2(a) and 2(b) are explanatory diagrams showing a configuration of a gas detecting element 3 used as a main part of the combustible gas detecting apparatus 1. FIG. 2(a) is a plan view (also showing a part of an internal configuration), and FIG. 2(b) is a sectional view taken on line A-A in FIG. 2(a).

Configuration

The combustible gas detecting apparatus 1 is an apparatus for detecting concentration of a combustible gas using the gas detecting element 3 of a heat conduction type and, for example, is installed inside a fuel-cell vehicle and is used for the purpose etc. of detecting a leak of hydrogen.

As shown in FIG. 1, the combustible gas detecting apparatus 1 includes a control circuit 5 for driving and controlling the gas detecting element 3 (see FIG. 2), a microcomputer 7 which generates a switching signal CG1 for controlling an operation of the control circuit 5 and which also executes various processing including at least processing (gas concentration computation processing) for computing gas concentration of a combustible gas included in a detected gas based on output voltages (detection signals) V1, VT obtained from the control circuit 5, and a starting switch 9 for starting and stopping the control circuit 5 and the microcomputer 7 by connecting and disconnecting a power source supply path from a DC power source Vcc (for example, 5 V) to the combustible gas detecting apparatus 1.

In addition, the control circuit 5 (but excluding a heating resistor 34 and a temperature measurement resistor 35 described below), the microcomputer 7 and the starting switch 9 are constructed on a single circuit substrate, and the gas detecting element 3 is constructed separately from this single circuit substrate.

Gas Detecting Element

Next, the gas detecting element 3 will be described.

Figure 2:
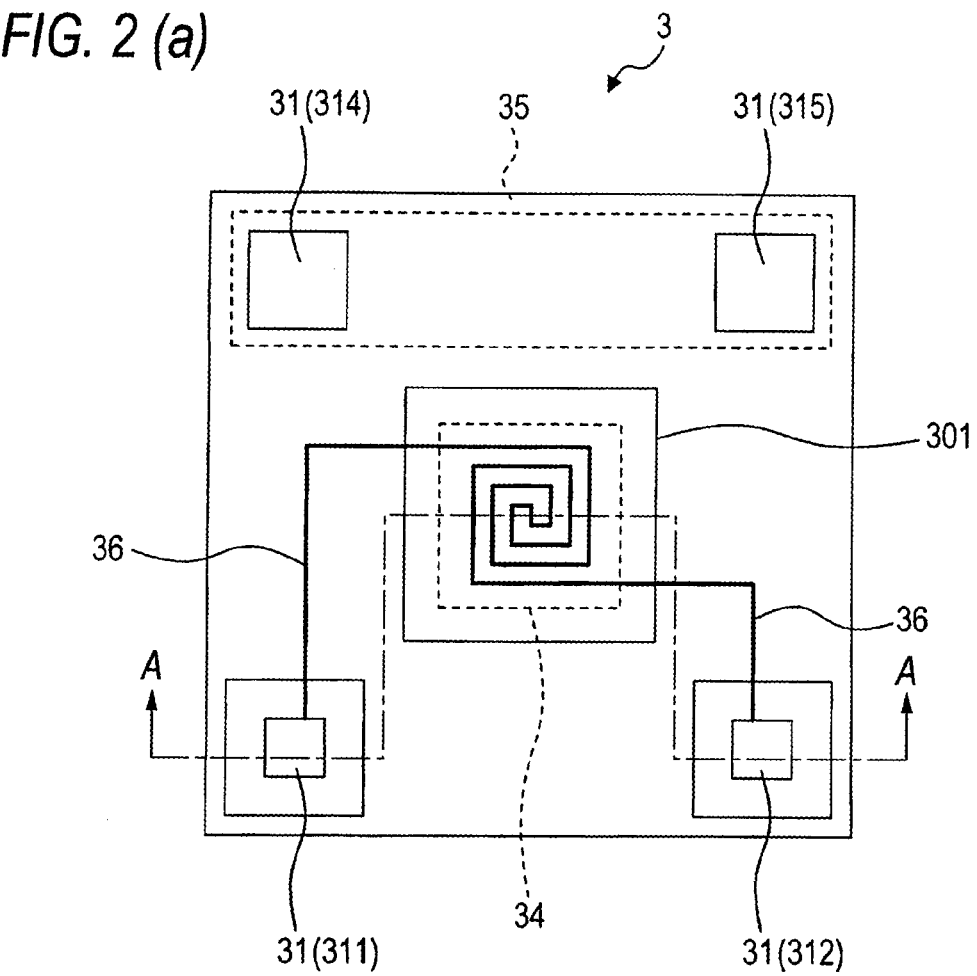
FIGS. 2(a) and 2(b) are explanatory diagrams showing a configuration of a gas detecting element of the combustible gas detecting apparatus.
Figure 2:
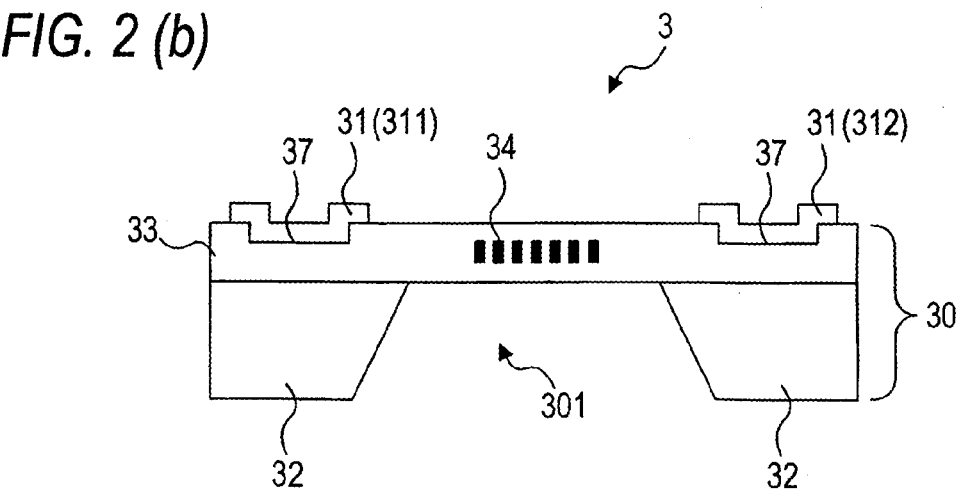

As shown in FIG. 2, the gas detecting element 3 includes a base 30 with a flat plate shape, and plural electrodes 31 are formed on one surface (hereinafter called a "front surface") of the base 30, and on the other surface (hereinafter called a "back surface"), one recess 301 is formed along one direction of the base 30 in the vicinity of the center of the base 30.

In addition, the gas detecting element 3 is about several-by-several mm (for example, three-by-three mm) in size, and is manufactured by, for example, a micromachining technique (micromachining processing) using a substrate made of silicon.

The electrodes 31 comprise two electrodes 311, 312 (hereinafter also called a "first electrode group") arranged along one side (a lower side in FIG. 2(a)) of the base 30, and two electrodes 314, 315 (hereinafter also called a "second electrode group") arranged along the other side (an upper side in FIG. 2(a)). The electrodes 312, 315 of these electrodes are also called "ground electrodes" hereinafter. Also, as a material constructing the electrodes 31, for example, aluminum (Al) or gold (Au) is used.

The base 30 includes a substrate 32 made of silicon and an insulating layer 33 formed on one surface of the substrate 32.

The base 30 has a diaphragm structure in which the recess 301 is formed by removing a part of the substrate 32 so as to expose the insulating layer 33 partially (substantially a square herein). That is, in the base 30, the side (the portion in which the substrate 32 is not removed) of the insulating layer 33 is used as the front surface of the base 30 and the side (including the portion in which a part of the substrate 32 is removed) of the substrate 32 is used as the back surface of the base 30.

In the insulating layer 33, the linear heating resistor 34 wired in a spiral shape is buried in a region exposed to the back surface of the base 30 by the recess 301 and also, the temperature measurement resistor 35 used in temperature measurement is buried along a long side of the base 30 of the side on which the second electrode group 314, 315 is formed.

In addition, the insulating layer 33 may be formed of a single material or may be formed so as to have plural layers using different materials. Also, as an insulating material constructing the insulating layer 33, for example, silicon oxide ($SiO_2$) or silicon nitride ($Si_3N_4$) is used.

The heating resistor 34 is made of a conductive material with a large temperature resistance coefficient in which a resistance value changes according to a change in temperature of the heating resistor itself and also, the temperature measurement resistor 35 is made of a conductive material in which electrical resistance changes in proportion to temperature (a resistance value increases with increasing temperature in the present embodiment). However, both of the heating resistor 34 and the temperature measurement resistor 35 are formed of the same resistance material (platinum (Pt) in the present embodiment).

Then, the heating resistor 34 is connected to the first electrode group 311, 312 through wiring 36 and a wiring film 37 buried in the same plane as a plane in which the heating resistor 34 is formed, and the temperature measurement resistor 35 is connected to the second electrode group 314, 315 through a wiring film (not shown) buried in the same plane as a plane in which the temperature measurement resistor 35 is formed.

In addition, as a material constructing the wiring 36 or the wiring film 37, the same resistance material as that of the heating resistor 34 and the temperature measurement resistor 35 is used. Also, connection between the electrodes 31 formed on the front surface of the base 30 and the wiring film 37 formed in the inside of the base 30 (the insulating layer 33) is made by contact holes (connected conductors).

That is, the heating resistor 34 makes connection so that one end conducts to the electrode 311 and the other end conducts to the ground electrode 312, and the temperature measurement resistor 35 makes connection so that one end conducts to the electrode 314 and the other end conducts to the ground electrode 315.

The gas detecting element 3 constructed as described above is used in a state arranged so as to be exposed to a detected atmosphere.

Control Circuit

Next, a configuration of the control circuit 5 will be described.

As shown in FIG. 1, the control circuit 5 includes an energization control circuit 50 for energizing the heating resistor 34 and outputting a detection signal V1 corresponding to a voltage across the heating resistor 34, and a temperature regulating circuit 80 for energizing the temperature measurement resistor 35 and outputting a temperature detection signal VT indicating a temperature of the detected atmosphere.

Energization Control Circuit

The energization control circuit 50 includes a bridge circuit (Wheatstone bridge circuit) 51 configured to include the heating resistor 34, an amplifying circuit 53 for amplifying a potential difference detected by the bridge circuit 51, and a current regulating circuit 55 for increasing or decreasing a current flowing through the bridge circuit 51 according to an output of the amplifying circuit 53.

The current regulating circuit 55 is connected to a power source line for supplying the DC power source Vcc to the bridge circuit 51, and includes a transistor in which an energized state (on resistance) changes according to a regulation signal C which is the output of the amplifying circuit 53. Specifically, the current regulating circuit 55 is constructed so that as the regulation signal C becomes large, the on resistance becomes high and a current flowing through the bridge circuit 51 decreases and, reversely, as the regulation signal C becomes small, the on resistance becomes low and the current flowing through the bridge circuit 51 increases.

The amplifying circuit 53 comprises a well-known differential amplifying circuit constructed by an operational amplifier 531, fixed resistors 532, 533 respectively connected to a non-inverting input terminal and an inverting input terminal of the operational amplifier 531, a fixed resistor 534 connected in parallel between an output terminal and the inverting input terminal of the operational amplifier 531, and a capacitor 535.

That is, the amplifying circuit 53 is constructed so that when an input voltage of the non-inverting input terminal is higher than an input voltage of the inverting input terminal, the regulation signal C which is the output of the amplifying circuit 53 becomes large (and thus the current flowing through the bridge circuit 51 decreases) and, reversely, when the input voltage of the non-inverting input terminal is lower than the input voltage of the inverting input terminal, the regulation signal C becomes small (and thus the current flowing through the bridge circuit 51 increases).

The bridge circuit 51 includes the heating resistor 34, two fixed resistors 511, 512, and a variable resistance part 52 capable of switching a resistance value, and is constructed by connecting the fixed resistor 511 in series with the heating resistor 34 and connecting the fixed resistor 512 in series with the variable resistance part 52 and grounding each end PG of the sides of the heating resistor 34 and the variable resistance part 52 of each of the series circuits and connecting each end of the sides of the fixed resistors 511, 512 to the power source side (the current regulating circuit 55).

Then, a point P+ of connection between the fixed resistor 511 and the heating resistor 34 is connected to the non-inverting input terminal of the operational amplifier 531 through the fixed resistor 532, and a point P− of connection between the fixed resistor 512 and the variable resistance part 52 is connected to the inverting input terminal of the operational amplifier 531 through the fixed resistor 533. Further, a potential of the connection point P+ is constructed so as to be supplied to the microcomputer 7 as the detection signal V1.

Also, the variable resistance part 52 includes two fixed resistors (a first fixed resistor 521, a second fixed resistor 522) with different resistance values, and a changeover switch part 520 (that is, a pair of changeover switches of a first changeover switch 523 and a second changeover switch 524) for effectively operating any one of the first and second fixed resistors 521, 522 according to the switching signal CG1 from the microcomputer 7, and is constructed so that a balance (balanced state) of the bridge circuit 51 can be changed by switching a resistance value of the variable resistance part 52 by both of the changeover switches 523, 524.

Specifically, the first changeover switch 523 performs on-off switching of a state of energizing the first fixed resistor 521, and the second changeover switch 524 performs on-off switching of a state of energizing the second fixed resistor 522.

In addition, the first fixed resistor 521 has a resistance value in which the heating resistor 34 becomes a first set temperature CH (for example, 400° C.) of the high temperature side, and the second fixed resistor 522 has a resistance value in which the heating resistor 34 becomes a second set temperature CL (for example, 300° C.) of the low temperature side set lower than the first set temperature CH. Therefore, the first changeover switch 523 is a contact point H at which the heating resistor 34 is switched to the high temperature side, and the second changeover switch 524 is a contact point L at which the heating resistor 34 is switched to the low temperature side.

Particularly in the present embodiment, as described below in detail, the detection signal V1 is constructed so as to be inputted to a first amplifying circuit 101 and a second amplifying circuit 102 and also, a first offset circuit 103 and a second offset circuit 104 for setting different offset voltages are respectively connected to the first amplifying circuit 101 and the second amplifying circuit 102. In addition, an output voltage (VH') of the first amplifying circuit 101 and an output voltage (VL') of the second amplifying circuit 102 are respectively constructed so as to be inputted to the microcomputer 7.

In the energization control circuit 50 constructed as described above, basically, the amplifying circuit 53 and the current regulating circuit 55 regulate a current flowing through the bridge circuit 51 so that a potential difference occurring between the connection points P+ and P− becomes zero when energization of the bridge circuit 51 from the DC power source Vcc is started. Consequently, a resistance value (and thus temperature) of the heating resistor 34 is controlled at a constant value (and thus the first set temperature CH or the second set temperature CL) determined by the variable resistance part 52.

Specifically, when the content of a combustible gas in a detected atmosphere changes and the amount of heat drawn by the combustible gas becomes higher than the amount of heat generated by the heating resistor 34, the resistance value of the heating resistor 34 decreases due to a decrease in temperature of the heating resistor 34. In reverse, when the amount of heat drawn by the combustible gas becomes lower than the amount of heat generated by the heating resistor 34, the resistance value of the heating resistor 34 increases due to an increase in temperature of the heating resistor 34.

On the other hand, the amplifying circuit 53 and the current regulating circuit 55 maintain the resistance value (and thus temperature) of the heating resistor 34 at a constant size by increasing the current flowing through the bridge circuit 51 and thus the amount of heat generated by the heating resistor 34 when the resistance value of the heating resistor 34 decreases and, reversely, by decreasing the current flowing through the bridge circuit 51 and thus the amount of heat generated by the heating resistor 34 when the resistance value of the heating resistor 34 increases.

That is, as described below in detail, the amount of heat (further the amount of heat drawn by the combustible gas) necessary to maintain magnitude of a current flowing through the heating resistor 34, namely, the temperature (and thus the resistance value) of the heating resistor 34 at a constant value is obtained from the detection signal V1 (specifically, the output voltages VH', VL' of the first and second amplifying circuits 101, 102) indicating the potential of the connection point P+, and the amount of heat becomes a magnitude corresponding to gas concentration, so that the gas concentration of the combustible gas is obtained from the detection signal V1 (specifically, VH1, VL1). In addition, specifically, correction is made using humidity H in the detected atmosphere in the case of calculating the gas concentration, and this will be described below with reference to "gas concentration computation processing."

Temperature Measuring Circuit

Next, the temperature regulating circuit 80 includes a bridge circuit (Wheatstone bridge circuit) 81 configured to include the temperature measurement resistor 35, and an amplifying circuit 83 for amplifying a potential difference obtained from the bridge circuit 81.

The amplifying circuit 83 comprises a well-known differential amplifying circuit constructed by an operational amplifier 831, fixed resistors 832, 833 respectively connected to a non-inverting input terminal and an inverting input terminal of the operational amplifier 831, a fixed resistor 834 connected in parallel between an output terminal and the inverting input terminal of the operational amplifier 831, and a capacitor 835.

The bridge circuit 81 includes the temperature measurement resistor 35 and three fixed resistors 811, 812, 813. The bridge circuit 81 is constructed by connecting the fixed resistor 811 in series with the temperature measurement resistor 35 and connecting the fixed resistor 812 in series with the fixed resistor 813 and grounding each end of the sides of the temperature measurement resistor 35 and the fixed resistor 813 of each of the series circuits and connecting each end of the sides of the fixed resistors 811, 812 to the power source (Vcc).

Then, a point P− of connection between the fixed resistor 811 and the temperature measurement resistor 35 is connected to the non-inverting input terminal of the operational amplifier 831 through the fixed resistor 833, and a point P+ of connection between the fixed resistor 812 and the fixed resistor 813 is connected to the inverting input terminal of the operational amplifier 831 through the fixed resistor 832. Also, an output of the operational amplifier 831 is constructed so as to be supplied to the microcomputer 7 as the temperature detection signal VT.

In the temperature measurement resistor 35, a temperature of the detected atmosphere to which the gas detecting element 3 is exposed is set so that the temperature detection signal VT becomes a reference value at the time of a preset reference temperature.

Then, with a change in temperature of the detected atmosphere, a resistance value of the temperature measurement resistor 35 changes and thereby, a potential difference occurs and an amplification of this potential difference is outputted as the temperature detection signal VT.

In addition, in each of the electrodes 31 (311, 312, 314, 315) of the gas detecting element 3 in connection between the gas detecting element 3 and the control circuit 5, the electrode 311 is connected to the connection point P+ of the energization control circuit 50 and the electrode 314 is connected to the connection point P− of the temperature regulating circuit 80 and the electrodes 312, 315 are connected to a ground line common to the control circuit 5.

Microcomputer

The microcomputer 7 is well-known unit including a storage device (ROM, RAM, etc.) for storing various data or programs for executing gas concentration computation processing etc., a CPU for executing the programs stored in this storage device, IO ports for inputting and outputting various signals, a timer for timing, etc.

In the discussion provided below, a signal level (i.e., a voltage obtained by predetermined computation described below from the output voltage VH' of the first amplifying circuit 101) of the detection signal V1 detected at the time of the first set temperature CH (400° C.) shall be called a voltage VH1 at high temperature, and a signal level (i.e., a voltage obtained by predetermined computation described below from the output voltage VL' of the second amplifying circuit 102) of the detection signal V1 detected at the time of the second set temperature CL (300° C.) shall be called a voltage VL1 at low temperature, and a signal level of the temperature detection signal VT read out of the temperature regulating circuit 80 shall be called a temperature voltage VT.

Then, at least temperature conversion data indicating a correlation between the temperature voltage VT and an environmental temperature T in the detected atmosphere, humidity conversion data indicating a correlation among the voltage VH1 at high temperature, the voltage VL1 at low temperature, the temperature voltage VT and the humidity H in the detected atmosphere, and concentration conversion data indicating a correlation between gas concentration X of the combustible gas and the voltage VH1 at high temperature or the voltage VL1 at low temperature (the voltage VH1 at high temperature is used in the present embodiment) are stored in the storage device. Also, an amplification factor and an offset voltage (described below) are stored. In addition, each of the conversion data is specifically made of map data for conversion, a calculation formula for conversion, etc. and is previously created based on data obtained by experiment, etc.

In addition, map data for voltage ratio conversion indicating a correlation between the environmental temperature T (and thus the temperature voltage VT) and a voltage ratio VC(0) (described below), and map data for humidity conversion indicating a correlation between the humidity H and a voltage ratio difference $\Delta$VC (described below) are included in the humidity conversion data. Further, map data for conversion of the voltage at high temperature indicating a correlation between the environmental temperature T and a voltage VH1(0) at high temperature (described below), map data for humidity voltage change conversion indicating a correlation among the voltage VH1 at high temperature, the humidity H and a change $\Delta$VH1(H) in the voltage at high temperature (described below), and map data for gas sensitivity conversion indicating a correlation among the environmental temperature T, the voltage VH1 at high temperature and gas sensitivity G(VT) (described below) are included in the concentration conversion data.

Next, the first and second amplifying circuits 101, 102 and the first and second offset circuits 103, 104, which are main parts of the present embodiment will be described in detail.

Figure 3:
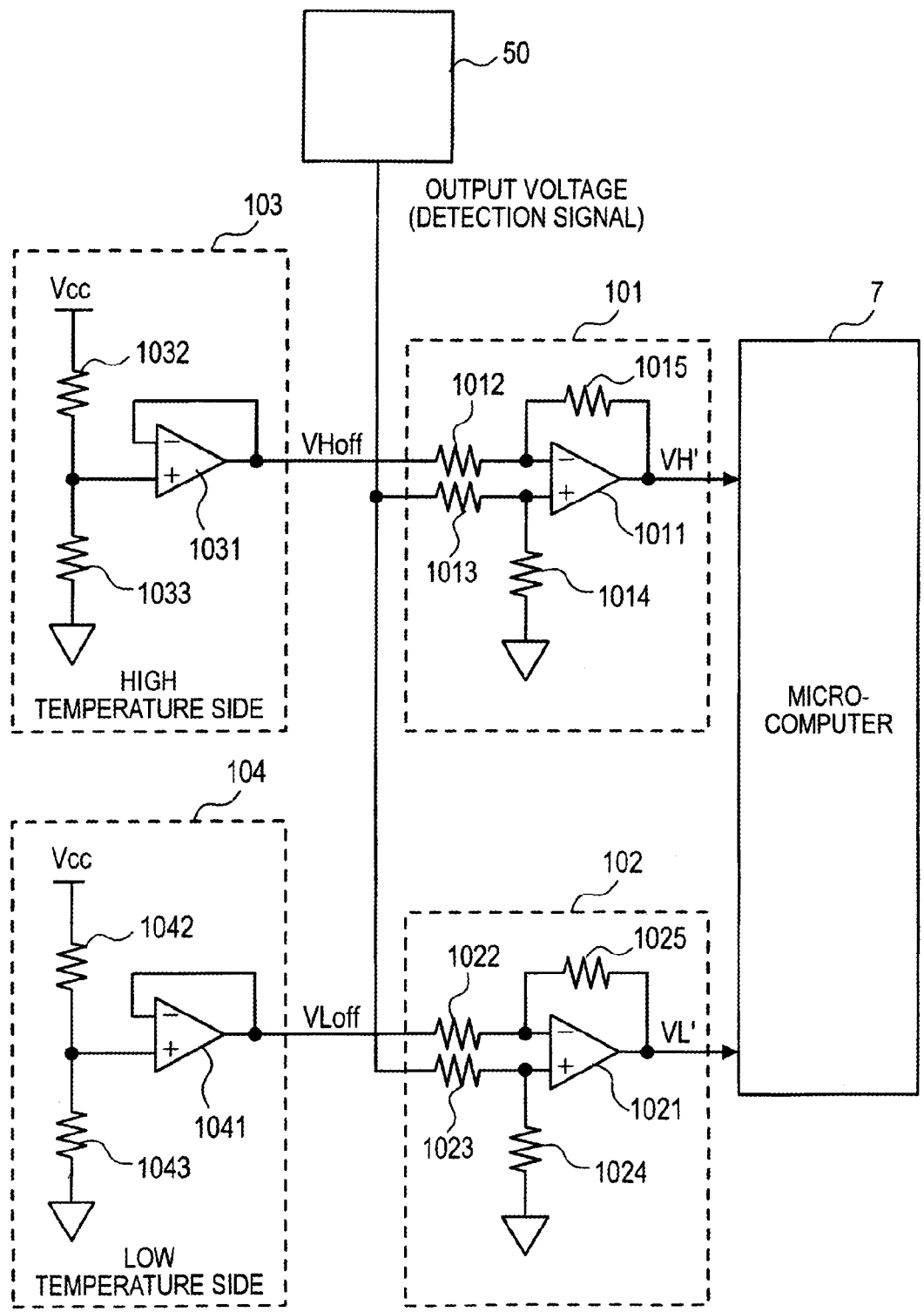
FIG. 3 is an explanatory diagram showing an offset circuit and an amplifying circuit of the combustible gas detecting apparatus.

In the combustible gas detecting apparatus 1 of the present embodiment, the first amplifying circuit 101, which is a differential amplifying circuit of the side of the first set temperature CH (that is, high temperature side of 400° C.), the second amplifying circuit 102, which is a differential amplifying circuit of the side of the second set temperature CL (that is, low temperature side of 300° C.), the first offset circuit 103, which is an offset circuit of the side of 400° C., and the second offset circuit 104, which is an offset circuit of the side of 300° C., are connected to a circuit ranging from the energization control circuit 50 to the microcomputer 7 as shown in FIG. 3 in addition to the basic configuration described above.

Specifically, the first amplifying circuit 101 comprises a well-known differential amplifying circuit constructed by an operational amplifier 1011, a fixed resistor 1012 connected to an inverting input terminal of the operational amplifier 1011, a fixed resistor 1013 connected to a non-inverting input terminal, a fixed resistor 1014 (grounded), and a fixed resistor 1015 connected in parallel between an output terminal and the inverting input terminal of the operational amplifier 1011.

In addition, an amplification factor in this first amplifying circuit 101 is set at M (for example, five times).

Similarly, the second amplifying circuit 102 comprises a well-known differential amplifying circuit constructed by an operational amplifier 1021, a fixed resistor 1022 connected to an inverting input terminal of the operational amplifier 1021, a fixed resistor 1023 connected to a non-inverting input terminal, a fixed resistor 1024 (grounded), and a fixed resistor 1025 connected in parallel between an output terminal and the inverting input terminal of the operational amplifier 1021. In addition, an amplification factor in this second amplifying circuit 102 is set at N (for example, six times).

Also, the first offset circuit 103 includes an operational amplifier 1031 and fixed resistors 1032, 1033 for dividing the power supply voltage Vcc (at a voltage dividing point), and an output terminal of the operational amplifier 1031 is connected to an inverting input terminal and the voltage dividing point is connected to a non-inverting input terminal of the operational amplifier 1031. This first offset circuit 103 sets a first offset voltage (an offset voltage of the high temperature side) VHoff in which the power supply voltage is divided according to a resistance ratio of the fixed resistors 1032, 1033.

Similarly, the second offset circuit 104 includes an operational amplifier 1041 and fixed resistors 1042, 1043 for dividing the power supply voltage Vcc (at a voltage dividing point), and an output terminal of the operational amplifier 1041 is connected to an inverting input terminal and the voltage dividing point is connected to a non-inverting input terminal of the operational amplifier 1041. This second offset circuit 104 sets a second offset voltage (an offset voltage of the low temperature side) VLoff in which the power supply voltage is divided according to a resistance ratio of the fixed resistors 1042, 1043.

Then, the inverting input terminal side of the operational amplifier 1011 of the first amplifying circuit 101 is connected to the output side of the first offset circuit 103 and also, the non-inverting input terminal side is connected to the output side (side to which the detection signal V1 is outputted) of the energization control circuit 50.

Similarly, the inverting input terminal side of the operational amplifier 1021 of the second amplifying circuit 102 is connected to the output side of the second offset circuit 104 and also, the non-inverting input terminal side is connected to the output side (side to which the detection signal V1 is outputted) of the energization control circuit 50.

Therefore, in the first amplifying circuit 101, a potential difference between the output voltage VHoff of the first offset circuit 103 and the output voltage V1 of the energization control circuit 50, namely, a difference obtained by subtracting the first offset voltage (for example, 3 V) from the output voltage (for example, 3.5 V) is amplified, and a voltage VH' after its amplification is outputted to the side of the microcomputer 7.

Similarly, in the second amplifying circuit 102, a potential difference between the output voltage VLoff of the second offset circuit 104 and the output voltage V1 of the energization control circuit 50, namely, a difference obtained by subtracting the second offset voltage (for example, 2.2 V) from the output voltage (for example, 2.5 V) is amplified, and a voltage VL' after its amplification is outputted to the side of the microcomputer 7.

Next, a principle in which measurement accuracy is improved by the combustible gas detecting apparatus 1 of the configuration mentioned above will be described briefly.

Figure 4:
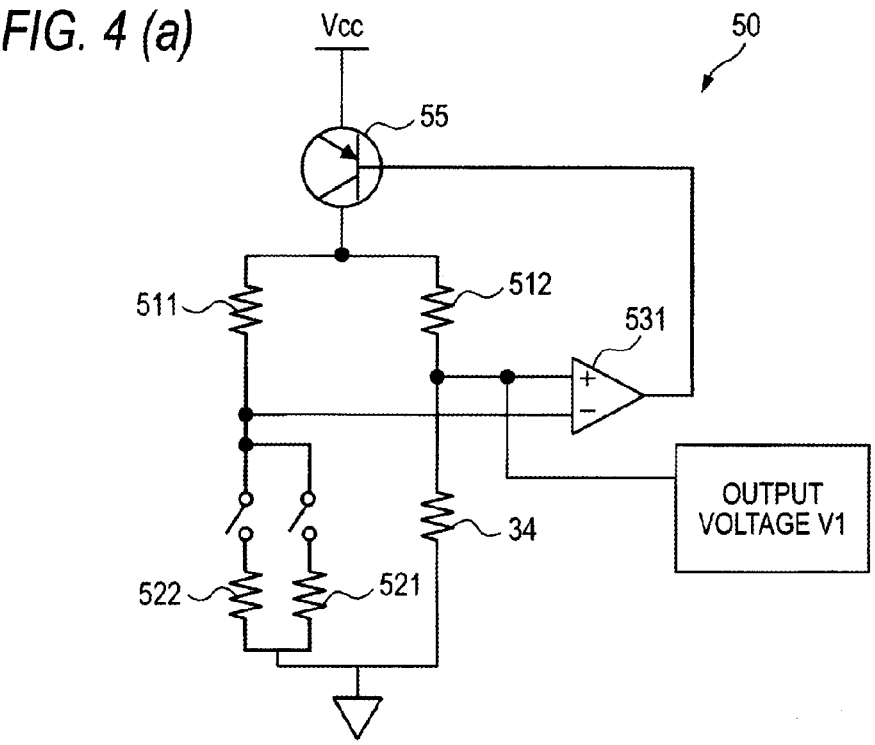
FIG. 4(a) is an explanatory diagram showing a main part of an energization control circuit.
FIG. 4(b) is a graph showing a relation between hydrogen concentration and an output voltage.
FIG. 4(c) is a graph showing a relation between ambient temperature and an output voltage.
Figure 4:
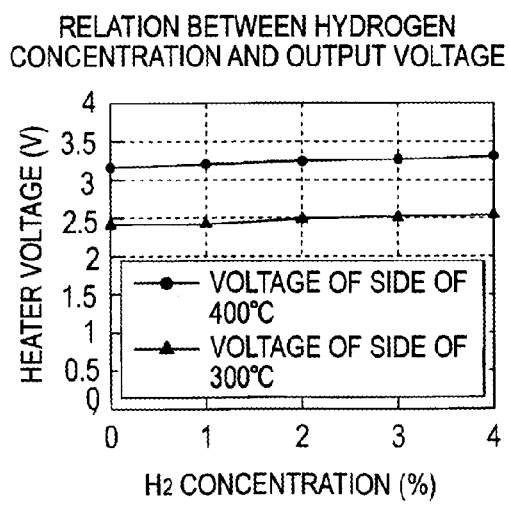
Figure 4:
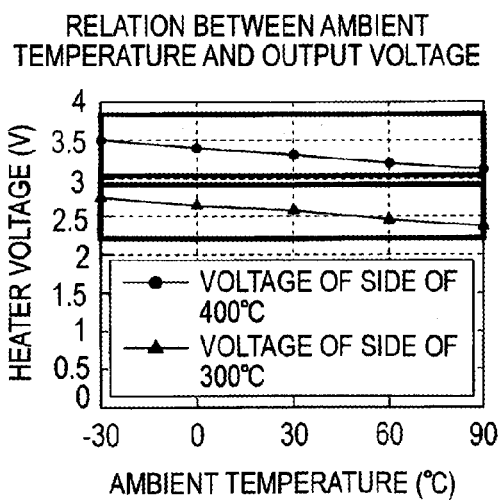

The energization control circuit 50 is schematically shown in FIG. 4(a) and the output voltage (detection signal) V1 of the energization control circuit 50 is obtained from the non-inverting input terminal side of the operational circuit 531.

That is, this output voltage V1 is a voltage (heater voltage) across the heating resistor 34 as is evident from FIG. 4(a).

Here, consider the case where the first and second amplifying circuits 101, 102 and the first and second offset circuits 103, 104 (described above) are absent and the output voltage V1 is inputted to the microcomputer 7 as it is. A relation between the output voltage V1 and hydrogen concentration is shown in FIG. 4(b). As shown in FIG. 4(b), although the heater voltage differs in the case of controlling the heating resistor (heater) 34 at 300° C. and the case of controlling the heating resistor 34 at 400° C., a change in heater voltage is slight when the hydrogen concentration changes. Specifically, sensitivity of the side of 400° C. is 43 mV per 1% of hydrogen and sensitivity of the side of 300° C. is 35 mV per 1% of hydrogen.

Similarly, a relation between the output voltage V1 and ambient temperature is shown in FIG. 4(c) and the case of controlling the heating resistor (heater) 34 at 300° C. differs from the case of controlling the heating resistor 34 at 400° C. in heater voltage, and it is found that a change in heater voltage is big with respect to a change in ambient temperature.

Therefore, it is not easy to detect the hydrogen concentration with high accuracy while correcting an influence etc. of the ambient temperature, from the in heater voltage which changes slightly according to the hydrogen concentration.

For example, when it is assumed that a power supply voltage is 5 V and the heater voltage is directly inputted to the microcomputer 7 with A/D resolution of 10 bits to make measurement, voltage resolution becomes 5000 mV/1024=5 mV. Therefore, resolution of the hydrogen concentration becomes (5 mV/43 mV)×10000=1160 ppm in the side of 400° C.

Also, consider the case of being amplified by an amplifier. Since it is necessary to be set at 5 V or less to be capable of being inputted to the microcomputer 7, when it is assumed that the maximum value of the heater voltage of the side of 400° C. is 4 V, amplification can be performed by only about 5 V/4 V=1.3 times. Therefore, the resolution of the hydrogen concentration becomes about 1160 ppm/1.3=890 ppm in the side of 400° C.

On the other hand, in the case of including the first and second amplifying circuits 101, 102 and the first and second offset circuits 103, 104 as shown in the present embodiment, when first and second offset voltages VHoff, VLoff are set in each of the sides of 400° C. and 300° C., high amplification can be performed and the resolution of the hydrogen concentration also becomes high.

Specifically, in the side of 400° C., when the first offset voltage VHoff is set at 3 V and the maximum value of the heater voltage of the side of 400° C. is set at 4 V and the power supply voltage is set at 5 V, for example, an amplification factor of 5 V/(4 V−3 V)=5 times can be achieved. In the side of 300° C., when the second offset voltage VLoff is set at 2.2 V and the maximum value of the heater voltage of the side of 300° C. is set at 3 V and the power supply voltage is set at 5 V, for example, an amplification factor of 5 V/(3 V−2.2 V)=6.3 times can be achieved. Therefore, the resolution of the hydrogen concentration also becomes, for example, 1160 ppm/5=230 ppm in the side of 400° C. and measurement of 500 ppm or less can be made.

By setting the two different offset voltages VHoff, VLoff in this manner, measurement of the hydrogen concentration etc. can be made with high accuracy.

Next, an operation in the combustible gas detecting apparatus 1 of the present embodiment will be described.

Gas Concentration Computation Processing

Below, gas concentration computation processing executed by a CPU of the microcomputer 7 will be described with reference to flowcharts shown in FIGS. 5 and 6.

In addition, the following offset voltages and amplification factors are previously inputted to the microcomputer 7.

Offset voltage of side of 400° C.: VHoff
Offset voltage of side of 300° C.: VLoff
Amplification factor of side of 400° C.: M
Amplification factor of side of 300° C.: N When power feeding is started from the DC power source Vcc by turning on the starting switch 9, the microcomputer 7 is activated and after each part of the microcomputer 7 is initialized, the gas concentration computation processing is started.

In addition, computation for obtaining gas concentration X includes a method for obtaining the gas concentration X from one or both of the voltage VL1 at low temperature and the voltage VH1 at high temperature using concentration conversion data and further obtaining the environmental temperature T from the temperature voltage VT using temperature conversion data and correcting the gas concentration X which is a computation result using only the environmental temperature T which is similarly a computation result, but the gas concentration X shall herein be obtained using the humidity H in addition to the environmental temperature T.

Figure 5:
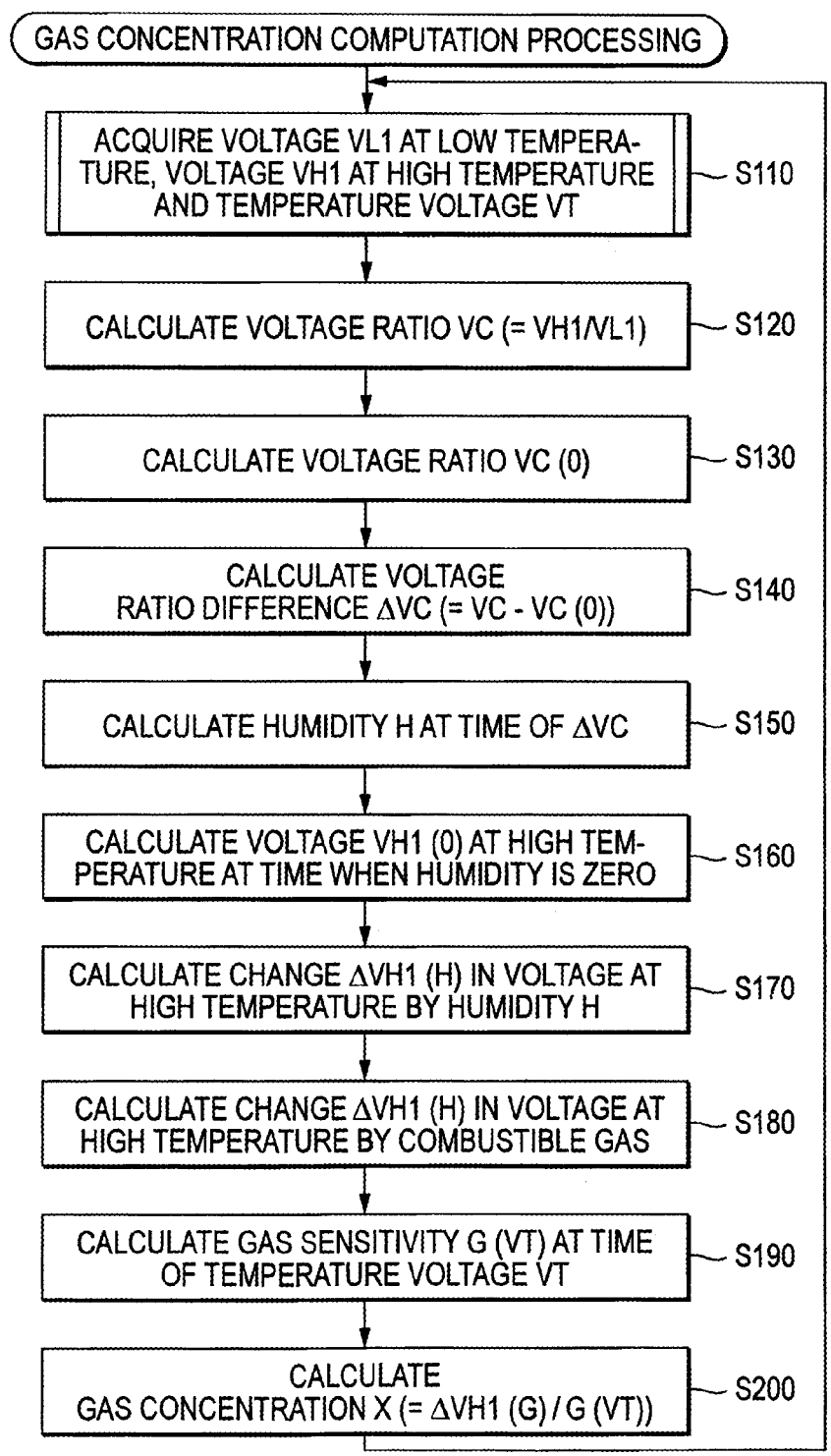
FIG. 5 is a flowchart showing the contents of gas concentration computation processing.

As shown in FIG. 5, when the present processing (gas concentration computation processing) is executed, the voltage VL1 at low temperature and the voltage VH1 at high temperature are first acquired from the energization control circuit 50 and also the temperature voltage VT is acquired from the temperature regulating circuit 80 in S110.

Below, control and processing in the case of acquiring the voltage VL1 at low temperature and the voltage VH1 at high temperature will be described in detail.

In the case of acquiring the voltage VL1 at low temperature and the voltage VH1 at high temperature, control in which a resistance value of the bridge circuit 51, namely, a set temperature of the heating resistor 34 is held at the second set temperature CL by the switching signal CG1 during a certain cycle time TW (hereinafter called a "low-temperature measurement period") and thereafter setting is switched and the set temperature is again held at the first set temperature CH during a certain cycle time TW (hereinafter called a "high-temperature measurement period") is performed.

Specifically, an operation for turning off the second changeover switch 524 (contact point L) while turning on the first changeover switch 523 (contact point H) is maintained over a high-temperature set period, namely, an operation for connecting the first fixed resistor 521 (for high temperature) as a resistor of the bridge circuit 51 is maintained over the high-temperature set period and, thereby, the temperature is held at the first set temperature CH.

Then, an operation for turning on the second changeover switch 524 while turning off the first changeover switch 523 after the end of the high-temperature set period is maintained over a low-temperature set period, namely, an operation for connecting the second fixed resistor 522 (for low temperature) as a resistor of the bridge circuit 51 is maintained over the low-temperature set period and thereby, the temperature is held at the second set temperature CL.

Then, such switching operations (switching control) of the switches are repeated every cycle period TW. Consequently, the temperature of the heating resistor 34 changes alternately. That is, a predetermined high temperature (400° C.) is maintained for the high-temperature set period, and a predetermined low temperature (300° C.) (lower than C2) is maintained for the low-temperature set period.

Figure 6:
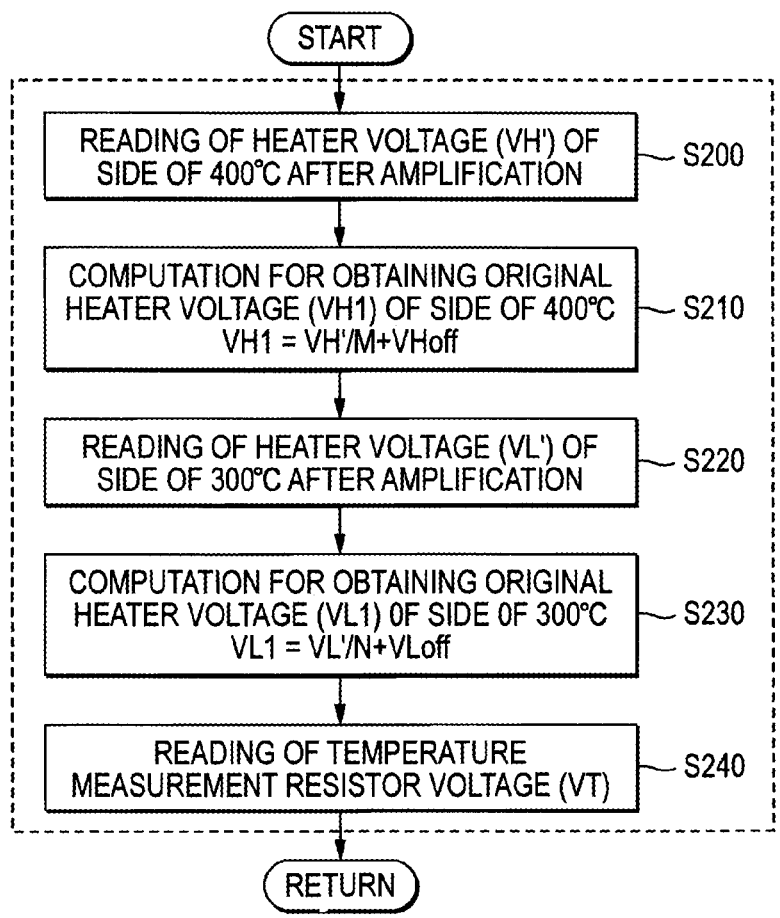
FIG. 6 is a flowchart showing processing in the case of calculating a voltage at low temperature and a voltage at high temperature.

Therefore, in the present embodiment, processing shown in FIG. 6 is performed with the operations described above.

Specifically, in S200 of FIG. 6, a heater voltage VH' after amplification outputted from the first amplifying circuit 101 is read for the high-temperature set period of 400° C.

In S210, computation for obtaining the original heater voltage VH1 of the side of 400° C. is performed by the following formula (1). Processing for returning the amplified voltage to the original state and also returning the subtracted first offset voltage VHoff to the original state is performed.

$$VH1 = VH'/M + VHoff \qquad (1)$$

In S220, a heater voltage VL' after amplification outputted from the second amplifying circuit 102 is read for the high-temperature set period of 300° C.

In S230, computation for obtaining the original heater voltage VL1 of the side of 300° C. is performed by the following formula (2).

$$VL1 = VL'/N + VLoff \qquad (2)$$

In S240, the temperature voltage (temperature measurement resistor voltage) VT is read from the temperature regulating circuit 80.

Then, processing of S120 downward is performed by returning to FIG. 5 after the processing shown in FIG. 6.

Specifically, in S120 of FIG. 5, the voltage ratio VC is calculated using the voltage VL1 at low temperature and the voltage VH1 at high temperature acquired in S110 as input values of the following formula (3).

$$VC = VH1/VL1 \qquad (3)$$

Also in parallel with this, in S130, gas concentration X and a voltage ratio VC(0) at the time when humidity H is zero at the environmental temperature T (and thus the temperature voltage VT) are calculated based on the map data for voltage ratio conversion and the temperature voltage VT acquired in S110.

Then, in S140, the voltage ratio difference ΔVC at the environmental temperature T (and thus the temperature voltage VT) is calculated using the voltage ratio VC calculated in S120 and VC(0) calculated in S130 as input values of the following formula (4).

$$\Delta VC = VC - VC(0) \qquad (4)$$

Then, in S150, the humidity H at the time of the voltage ratio difference ΔVC is calculated based on the map data for humidity conversion and the voltage ratio difference ΔVC calculated in S140.

Also in parallel with this, in S160, the gas concentration X and a voltage VH1(0) at high temperature at the time when the humidity H is zero at the environmental temperature T (and thus the temperature voltage VT) are calculated based on the map data for conversion of the voltage at high temperature, the temperature voltage VT and the voltage VH1 at high temperature acquired in S110.

Subsequently, in S170, the change ΔVH1(H) in the voltage at high temperature indicating the amount of change caused by the humidity H among the voltage VH1 at high temperature is calculated based on the map data for humidity voltage change conversion, the humidity H calculated in S150 and the voltage VH1 at high temperature acquired in S110.

Then, in S180, a change ΔVH1(G) in the voltage at high temperature indicating the amount of change caused by the combustible gas among the voltage VH1 at high temperature is calculated using the change ΔVH1(H) in the voltage at high temperature calculated in S170, the voltage VH1(0) at high temperature calculated in S160 and the voltage VH1 at high temperature acquired in S110 as input values of the following formula (5).

$$\Delta VH1(G) = VH1 - VH1(0) - \Delta VH1(H) \qquad (5)$$

Also in parallel with this, in S190, the gas sensitivity G(VT) indicating sensitivity (a unit is the reciprocal of the gas concentration X) to the combustible gas preset every the environmental temperature T (and thus the temperature voltage VT) in the voltage VH1 at high temperature is calculated based on the map data for gas sensitivity conversion, the temperature voltage VT and the voltage VH1 at high temperature acquired in S110.

Finally, in S200, the gas concentration X of the combustible gas is calculated using the gas sensitivity G(VT) calculated in S190 and the change ΔVH1(G) in the voltage at high temperature calculated in S180 as input values of the following formula (6), and the flowchart returns to S110.

$$X = \Delta VH1(G)/G(VT) \qquad (6)$$

In the present processing, thus, an energization path (energization path in the variable resistance part 52) from the point P− of connection between the fixed resistor 512 and the variable resistance part 52 to the end PG (ground side end in the variable resistance part 52) is switched from one side of the first and second fixed resistors 521, 522 to the other side by outputting the switching signal CG1 to the changeover switch part 520 every cycle time TW.

Consequently, the voltage VH' at high temperature and the voltage VL' at low temperature after amplification are obtained and also, the voltage VH1 at high temperature and the voltage VL1 at low temperature are calculated from the voltage VH' at high temperature and the voltage VL' at low temperature and further, the temperature voltage VT is acquired.

Then, the environmental temperature T is obtained from the temperature voltage VT and, further, the humidity H in the detected atmosphere is obtained from a ratio between the voltage VH1 at high temperature and the voltage VL1 at low temperature, and the gas concentration X is corrected using the environmental temperature T and the humidity H.

Effects

As described above, the combustible gas detecting apparatus 1 of the present embodiment includes the first and second amplifying circuits 101, 102 and the first and second offset circuits 103, 104.

The first offset circuit 103 sets the first offset voltage VHoff of the high temperature side, and the second offset circuit 104 sets the second offset voltage VLoff of the low temperature side. Also, in the first amplifying circuit 101, the first offset voltage VHoff is subtracted from the output voltage V1 from the energization control circuit 50, and the voltage VH' in which its differential voltage is amplified is inputted to the microcomputer 7. Similarly, in the second amplifying circuit 101, the second offset voltage VLoff is subtracted from the output voltage V1 from the energization control circuit 50, and the voltage VL' in which its differential voltage is amplified is inputted to the microcomputer 7. Further, the microcomputer 7 is constructed so as to calculate the voltage VH1 at high temperature and the voltage VL1 at low temperature from each of the amplified voltages VH', VL' by the formulas (1) and (2).

Consequently, even when the output voltage (heater voltage) from the heating resistor has a very small change in voltage, a proper offset voltage is set and, thereby, only the portion of change in voltage can suitably be taken out to be amplified at a large amplification factor. Hence, there is a remarkable effect of the capability of measuring hydrogen concentration with high accuracy by setting the large amplification factor even in the case of using the low-cost microcomputer 7.

Particularly, in the present embodiment, the amplified voltages VH', VL' can always be acquired from the first and second amplifying circuits 101, 102, so that the offset voltages corresponding to the respective temperatures (set temperatures) can always be set in the first and second amplifying circuits 101, 102 as compared with the case of adopting a configuration of switching to two different offset voltages using the microcomputer 7. Also in the present embodiment, the first and second amplifying circuits 101, 102 are constructed so as to set optimum amplification factors (amplification degrees) suitable to each of the heater voltages at different values. This enables measurement of the hydrogen concentration with higher accuracy in the present embodiment. Also, there is an advantage of the capability of simplifying control of the microcomputer 7 since the need for switching control etc. of the offset voltages is eliminated.

In addition, the amplification factors M, N may be set at the same value. Also, the magnitude of each of the offset voltages VHoff, VLoff could be set properly according to the amplification factor, or a change in the output voltage from the heating resistor 34 or the power supply voltage of the microcomputer 7.

In addition, in the present embodiment, the energization control circuit 50 corresponds to a control circuit, and the first offset circuit 103 corresponds to a first offset setting unit, and the second offset circuit 104 corresponds to a second offset setting unit, and the first amplifying circuit 101 corresponds to a first amplifying unit, and the second amplifying circuit 102 corresponds to a second amplifying unit.

Second Embodiment

Next, a second embodiment will be described, but description of the contents similar to those of the first embodiment is omitted.

A combustible gas detecting apparatus of the second embodiment is an apparatus for switching an offset voltage by control from a microcomputer.

Figure 7:
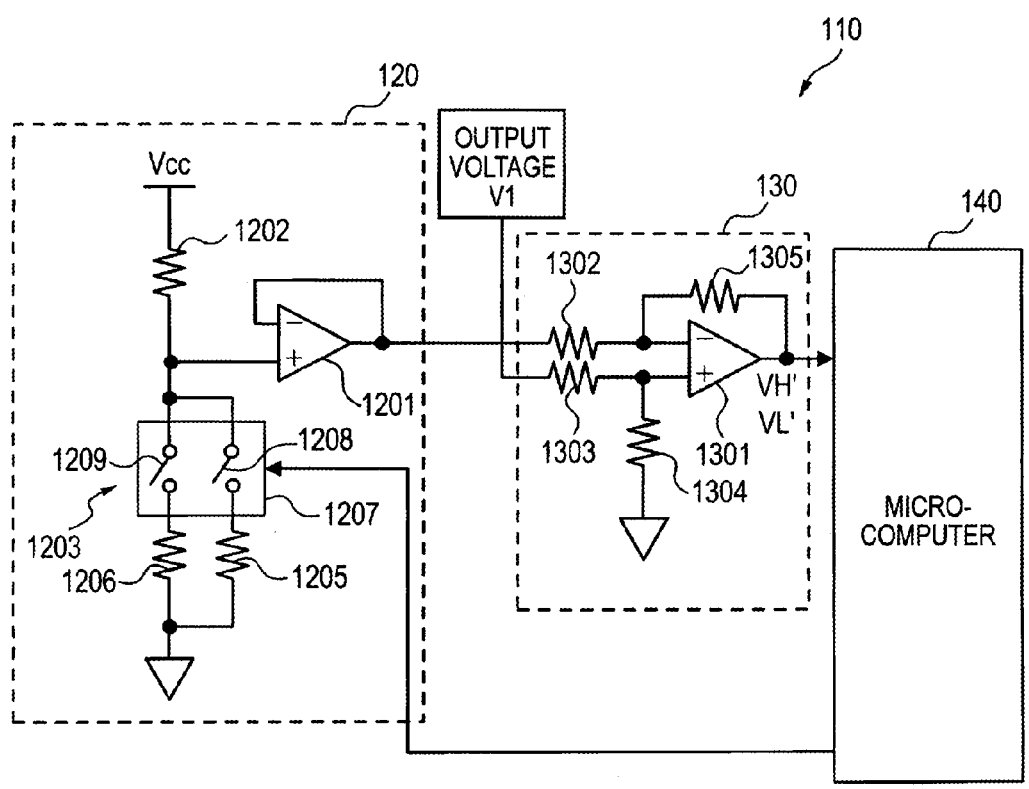
FIG. 7 is an explanatory diagram showing a main part of a combustible gas detecting apparatus of a second embodiment.

As shown in FIG. 7, a combustible gas detecting apparatus 110 of the second embodiment includes an energization control circuit, a bridge circuit, etc. like the first embodiment (the configuration similar to that of the first embodiment is not shown).

Particularly, the second embodiment includes an offset circuit 120 for setting two offset voltages VHoff, VLoff, an amplifying circuit 130 for amplifying a potential difference between the offset voltages VHoff, VLoff from the offset circuit 120 and an output voltage V1 from the energization control circuit, and a microcomputer 140.

The amplifying circuit 130 comprises a well-known differential amplifying circuit constructed by an operational amplifier 1301, a fixed resistor 1302 connected to an inverting input terminal of the operational amplifier 1301, a fixed resistor 1303 connected to a non-inverting input terminal, a fixed resistor 1304 (grounded), and a fixed resistor 1305 connected in parallel between an output terminal and the inverting input terminal of the operational amplifier 1301. In addition, an amplification factor in this amplifying circuit 130 is set at M (for example, five times).

Also, the offset circuit 120 includes an operational amplifier 1201, a fixed resistor 1202 and a switching resistance part 1203 for dividing a power supply voltage Vcc (at a voltage dividing point), and an output terminal of the operational amplifier 1201 is connected to an inverting input terminal and the voltage dividing point is connected to a non-inverting input terminal of the operational amplifier 1201.

The switching resistance part 1203 includes a fixed resistor 1205 (for high temperature), a fixed resistor 1206 (for low temperature) arranged in parallel, and a switch part 1207, and the switch part 1207 includes first and second changeover switches 1208, 1209 for turning on and off connection of each of the fixed resistors.

Particularly in the second embodiment, control for switching both of the changeover switches 1208, 1209 is performed by a control signal from the microcomputer 140.

Specifically, for a high-temperature measurement period, the first changeover switch 1208 is turned on (in a state of turning off the second changeover switch 1209) to connect the fixed resistor 1205 so that the first offset voltage VHoff corresponding to the time of high temperature can be outputted to the amplifying circuit 130.

Therefore, for the high-temperature measurement period, the amplifying circuit 130 amplifies a voltage obtained by subtracting this first offset voltage VHoff from the output voltage V1 from an energization control circuit 50, and this voltage VH' after amplification is inputted to the microcomputer 140.

Similarly, for a low-temperature measurement period, the second changeover switch 1209 is turned on (in a state of turning off the first changeover switch 1208) to connect the fixed resistor 1206 so that the second offset voltage VLoff corresponding to the time of low temperature can be outputted to the amplifying circuit 130.

Therefore, for the low-temperature measurement period, the amplifying circuit 130 amplifies a voltage obtained by subtracting this second offset voltage VLoff from the output voltage V1 from the energization control circuit 50, and this voltage VL' after amplification is inputted to the microcomputer 140.

In addition, values etc. of each of the fixed resistors are set so that each of the offset voltages VHoff, VLoff can be outputted in the case of switching both of the changeover switches 1208, 1209.

Also in the second embodiment, there is an effect similar to that of the first embodiment and also, one offset circuit 120 and one amplifying circuit 130 will suffice, so that there is an advantage of contributing to cost reduction.

Third Embodiment

Next, a third embodiment will be described, but description of the contents similar to those of the first embodiment is omitted.

A combustible gas detecting apparatus of the third embodiment is an apparatus for switching an offset voltage by control from a microcomputer.

Figure 8:
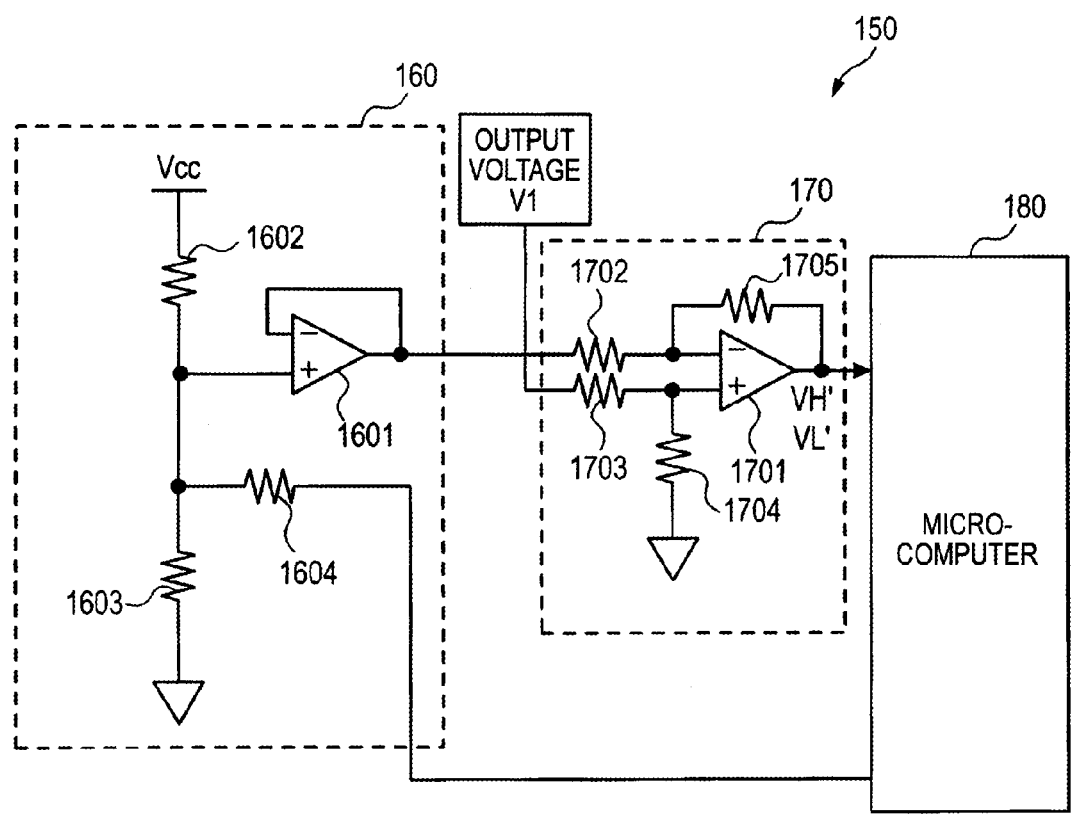
FIG. 8 is an explanatory diagram showing a main part of a combustible gas detecting apparatus of a third embodiment.

As shown in FIG. 8, a combustible gas detecting apparatus 150 of the third embodiment includes an energization control circuit, a bridge circuit, etc. like the first embodiment (the configuration similar to that of the first embodiment is not shown).

Particularly, the third embodiment includes an offset circuit 160 for setting two offset voltages VHoff, VLoff, an amplifying circuit 170 for amplifying a potential difference between the offset voltages VHoff, VLoff from the offset circuit 160 and an output voltage V1 from the energization control circuit, and a microcomputer 180.

The amplifying circuit 170 comprises a well-known differential amplifying circuit constructed by an operational amplifier 1701, a fixed resistor 1702 connected to an inverting input terminal of the operational amplifier 1701, a fixed resistor 1703 connected to a non-inverting input terminal, a fixed resistor 1704 (grounded), and a fixed resistor 1705 connected in parallel between an output terminal and the inverting input terminal of the operational amplifier 1701. In addition, an amplification factor in this amplifying circuit 170 is set at M (for example, five times).

Also, the offset circuit 160 includes an operational amplifier 1601, and fixed resistors 1602, 1603 for dividing a power supply voltage Vcc (at a voltage dividing point), and an output terminal of the operational amplifier 1601 is connected to an inverting input terminal and the voltage dividing point is connected to a non-inverting input terminal of the operational amplifier 1601.

Particularly in the third embodiment, a circuit ranging from the microcomputer 180 to the voltage dividing point is provided with a fixed resistor 1604, and a control signal from the microcomputer 180 is added to the voltage dividing point.

Specifically, for a high-temperature measurement period, a control signal (specifically, a voltage of 5 V) corresponding to the time of high temperature is outputted from the microcomputer 180 so that the first offset voltage VHoff corresponding to the time of high temperature can be outputted.

Therefore, for the high-temperature measurement period, one amplifying circuit 170 amplifies a voltage obtained by subtracting this first offset voltage VHoff from the output voltage V1 from an energization control circuit 50, and this voltage VH' after amplification is inputted to the microcomputer 180.

Similarly, for a low-temperature measurement period, a control signal (specifically, a voltage of 0 V) corresponding to the time of low temperature is outputted from the microcomputer 180 so that the second offset voltage VLoff corresponding to the time of low temperature can be outputted.

Therefore, for the low-temperature measurement period, the amplifying circuit 170 amplifies a voltage obtained by subtracting this second offset voltage VLoff from the output voltage V1 from an energization control circuit 50, and this voltage VL' after amplification is inputted to the microcomputer 180.

In addition, the control signals from the microcomputer 180 or values etc. of each of the fixed resistors are set so that each of the offset voltages VHoff, VLoff can be outputted.

Also in the third embodiment, there is an effect similar to that of the first embodiment and also, one offset circuit and one amplifying circuit will suffice, so that there is an advantage of contributing to cost reduction. Particularly, a switch for switching is not used, so that the cost is extremely low.

Experiment Example

Below, for example, the combustible gas detecting apparatus of the first embodiment and a combustible gas detecting apparatus (of Comparative Examples 1 and 2) beyond the scope of the invention are taken as examples and a difference between the apparatuses in voltage resolution is described.

In the combustible gas detecting apparatus (Example 1) of the first embodiment, A/D resolution of a microcomputer was set at 10 bits (1024), and a power supply voltage was set at 5 V, and the high temperature side and the low temperature side of a heating resistor were set at 400° C. and 300° C., and a first offset voltage VHoff was set at 3 V, and a second offset voltage VLoff was set at 2.2 V.

In this Example 1, when a heater voltage operating range is 3 to 4 V at the side of 400° C. and is 2.2 to 3 V at the side of 300° C., at the side of 400° C., an amplification factor is five times and the voltage resolution is 1 mV. Also, at the side of 300° C., the amplification factor is six times and the voltage resolution is 0.8 mV.

In Comparative Example 1, an output voltage from an energization control circuit is processed as it is by the microcomputer and gas concentration is measured. In addition, this Comparative Example 1 is similar to the first embodiment except that the first and second amplifying circuits 101, 102 and the first and second offset circuits 103, 104 are not included.

In this Comparative Example 1, when each of the numerical values (of the A/D resolution of the microcomputer, the power supply voltage, temperatures of the heating resistor and the heater voltage operating range) is set in a manner similar to Example 1, the amplification factor is 1 and the voltage resolution is 5 mV and this is inferior to the first embodiment.

In Comparative Example 2, an offset voltage is singly subtracted from an output voltage from an energization control circuit and its potential difference is amplified by a single amplifying circuit and its amplified voltage is processed by the microcomputer and gas concentration is measured. In addition, this Comparative Example 2 includes the energization control circuit and a temperature measuring circuit like the first embodiment.

In this Comparative Example 2, when each of the numerical values (of the A/D resolution of the microcomputer, the power supply voltage, temperatures of the heating resistor and the heater voltage operating range) is set in a manner similar to Example 1 and an offset voltage is set at 2 V, the amplification factor is 2.5 and the voltage resolution is 2.5 mV and this is inferior to the first embodiment.

Other Embodiment

Illustrative embodiments of the invention have been described above, but the invention is not limited to the illustrative embodiments described above, and can be implemented in various forms without departing from the gist of the invention. It should further be apparent to those skilled in the art that various changes in form and detail of the invention as shown and described above may be made. It is intended that such changes be included within the spirit and scope of the claims appended hereto.

(1) For example, in the illustrative embodiments described above, the combustible gas detecting apparatus for detecting a hydrogen gas is described, but an illustrative embodiment of the invention can be applied to detection of specified gases of helium, methane, etc. in addition to the hydrogen gas.

(2) Also, in the illustrative embodiments described above, the gas concentration X is calculated using the humidity H in the detected atmosphere, but the invention is not limited to this, and the gas concentration X may be configured to be calculated using at least a voltage across a heating resistor and a temperature voltage of a temperature measurement resistor.

(3) Further, an illustrative embodiment of the invention can be applied to detection of states of other gases in addition to detection of concentration etc. of the specified gases. An illustrative embodiment of the invention can be applied to, for example, a heat conductivity humidity sensor as described in JP-A-9-5284. Also in this case, an improvement in measurement accuracy can be expected by properly making setting of an offset voltage and amplification by an amplifying circuit.

This application is based on Japanese Patent Application No. 2011-070291 filed Mar. 28, 2011, the disclosure of which is incorporated herein by reference in its entirety.

What is claimed is:

1. A gas detecting apparatus comprising:
an electronic controller;
a heating resistor exposed to an atmosphere;
a control circuit for controlling the heating resistor to exhibit two different temperatures; and
an amplifying unit,
wherein an input offset voltage that is input to the amplifying unit is switched to any of two different offset voltages in response to a control signal from the electronic controller,
wherein the control circuit detects output voltages from the heating resistor corresponding to the two different temperatures,
wherein potential differences, which are obtained by subtracting respective ones of the two different offset voltages from corresponding ones of the detected output voltages, are amplified by the amplifying unit, and
wherein the electronic controller detects a state of a gas in the atmosphere based on the amplified potential differences.

2. A gas detecting apparatus comprising:
an electronic controller;
a heating resistor exposed to an atmosphere;
a control circuit for controlling the heating resistor to exhibit two different temperatures and detecting output voltages from the heating resistor corresponding to the two different temperatures;
a first offset setting unit which sets a first offset voltage corresponding to a first temperature of the two different temperatures;
a second offset setting unit which sets a second offset voltage corresponding to a second temperature of the two different temperatures;
a first amplifying unit which amplifies a first potential difference between the first offset voltage and a first output voltage of the detected output voltages, the first output voltage corresponding to the first temperature; and
a second amplifying unit which amplifies a second potential difference between the second offset voltage and a second output voltage of the detected output voltages, the second output voltage corresponding to the second temperature,
wherein the electronic controller detects a state of a gas in the atmosphere based on the amplified potential differences.

3. A method for detecting a state of a gas in an atmosphere, the method comprising:
exposing a heating element to the atmosphere;
controlling the heating element to exhibit a first temperature;
detecting a first output voltage from the heating element exhibiting the first temperature;
controlling the heating element to exhibit a second temperature;
detecting a second output voltage from the heating element exhibiting the second temperature;
setting a first offset voltage and a second offset voltage;
determining a first potential difference by subtracting the first offset voltage from the first output voltage;
determining a second potential difference by subtracting the second offset voltage from the second output voltage;
amplifying the first potential difference and the second potential difference; and
detecting the state of the gas based on the amplified first potential difference and the amplified second potential difference.

4. A gas detecting apparatus comprising:
an electronic controller;
a heating resistor configured to be exposed to an atmosphere and controlled by a control circuit to exhibit a first temperature and a second temperature, in response to the heating resistor exhibiting the first temperature, the heating resistor outputs a first voltage, and in response to the heating resistor exhibiting the second temperature, the heating resistor outputs a second voltage; and
an amplifying circuit configured to amplify a first potential difference and a second potential difference, the first potential difference being obtained by subtracting a first offset voltage from the first voltage and the second potential difference being obtained by subtracting a second offset voltage from the second voltage,
wherein the electronic controller detects a state of a gas in the atmosphere based on the first and second amplified potential differences.

* * * * *